United States Patent [19]

Urata et al.

[11] Patent Number: 4,906,927
[45] Date of Patent: Mar. 6, 1990

[54] EDDY CURRENT FLAW DETECTING APPARATUS AND METHOD THEREOF

[75] Inventors: Megumu Urata, Naka; Kazushige Tsukui, Mito, both of Japan

[73] Assignee: Nippon Nuclear Fuel Development Co., Ltd., Ibaraki, Japan

[21] Appl. No.: 261,997

[22] Filed: Oct. 25, 1988

[30] Foreign Application Priority Data

Nov. 9, 1987 [JP] Japan ................................. 62-281051

[51] Int. Cl.$^4$ ......................................... G01N 27/82
[52] U.S. Cl. ..................................... 324/238; 324/233
[58] Field of Search .............................. 324/234–243, 324/260–262

[56] References Cited

U.S. PATENT DOCUMENTS

| | | | |
|---|---|---|---|
| 1,129,584 | 2/1915 | Murphy | 324/238 |
| 2,957,129 | 10/1960 | Irwin | 324/238 |
| 2,997,645 | 8/1961 | Huddleston, Jr. et al. | 324/339 |
| 3,146,395 | 8/1964 | Quittner | 324/241 |
| 3,411,344 | 11/1968 | Lloyd | 324/238 X |
| 3,444,459 | 5/1969 | Prindle et al. | 324/242 |
| 4,480,225 | 10/1984 | Nance et al. | 324/238 |

FOREIGN PATENT DOCUMENTS 565248 8/1977 U.S.S.R. ............................. 324/240

Primary Examiner—Gerard R. Strecker
Assistant Examiner—Warren S. Edmonds
Attorney, Agent, or Firm—Antonelli, Terry & Wands

[57] ABSTRACT

An eddy current flaw detecting apparatus comprises a pair of detection coils each connected in adjoining arms of flaw detecting bridge circuit, the planes containing the pair of coils are arranged in parallel and inclined to the axis of a fuel clad pipe being examined at an inclination angle between 75° and 85° and an arrangement for rotating the fuel clad pipe relative to the pair of detection coils, when a flaw is detected while moving the fuel clad pipe relative to the pair of detection coils, to obtain a characteristic curve between a flaw signal output and turning angle in order to determine direction of the flaw, such as circumferential and axial, in comparison with characteristic curves between a flaw signal output and turning angle obtained in advance with respect to standard flaw testing pieces.

1 Claim, 4 Drawing Sheets

EDDY CURRENT FLAW DETECTING APPARATUS AND METHOD THEREOF

The present invention relates to a non-destructive testing apparatus and method thereof of workpieces by eddy current detecting techniques and is suitable, for example, for detecting flaws in fuel clad pipes for nuclear power generation.

BACKGROUND OF THE INVENTION

In a conventional eddy current flaw detecting apparatus and method, types of flaws, such as an external flaw, an internal flaw and a through hole flaw, in an object being examined are judged by a phase analysis method of flaw signals from a bridge circuit wherein the analyzed data are compared with those caused by flaws with a standard flaw testing piece obtained in advance while varying the phase angle $\Phi$ of a flaw signal processing unit of an eddy current flaw detecting apparatus, as shown in, for example, Eddy Current Flaw Detecting Test A (edited by Nihon Hihakai Kensa Kyokai (Japan Non-Destructive Inspection Society), 1977). In order to determine size of flaws by using the same flaw detecting apparatus, the relationship between the flaw signal output (V) and the size of a flaw, in depth thereof or in diameter of through hole, for each type of flaw in the standard flaw testing piece is obtained in advance, and the size of a flaw of an object being examined is determined comparing the obtained relationship with that in the standard flaw testing piece.

Although the position, type and size of a flaw of the workpieces can be determined by the above-described conventional apparatus and method, it was impossible to determined the direction of the flaw, in other words, whether the flaw is an axially orienting flaw or a circumferentially orienting flaw.

For example, when the object being examined is a fuel clad pipe for light-water type power reactor, if it is assumed that a rise in the inner pressure thereof would break the clad pipe, an axial flaw exerts a deleterious effect rather than a circumferential flaw. However, depending upon objects being examined, the circumferential flaw could be more deleterious. In summary, it is possible to judge the significance of a flaw by detecting the direction of the flaw in the workpieces.

U.S. Pat. No. 4,480,225 discloses a dual coil bobbin eddy current inspection probe connected in a bridge circuit for an eddy current flaw detecting apparatus wherein the planes containing the dual coils are arranged in non-parallel and in predetermined acute angles to the transverse axis of the probe such that the apparatus detects flaws in a tubular workpiece in a single scan. However the apparatus does not teach determination of flaw direction in the workpiece.

SUMMARY OF THE INVENTION

Accordingly, it is an object of the present invention to improve the above-described conventional apparatus and method and to provide an eddy current flaw detecting apparatus and method which are capable of determining the direction of a flaw in an object being examined.

The eddy current flaw detecting apparatus of the present invention provides a pair of detecting coils each being connected in adjoining arms of a bridge circuit therefor, the planes containing the pair of coils are in parallel and inclined to the longitudinal axis of an object being examined at an angle between 75° and 85°, and means for rotating the pair of coils relative to the object being examined when a flaw signals being detected at the bridge circuit in order to measure changes in magnitude of the flaw signal with respect to rotation angles and to compare the measured changes with those obtained in advance with respect to flaws of a standard flaw test piece.

The eddy current flaw detecting method of the present invention provides steps of moving an object being examined relative to and along with a pair of detecting coils each connected in adjoining arms of a bridge circuit of an eddy current detecting apparatus until the bridge circuit detects a flaw signal, the planes containing the pair of coils being arranged in parallel and inclined to the longitudinal axis of the object being examined at an inclination angle between 75° and 85°, and rotating the object being examined relative to the pair of coils when the bridge circuit detects the flaw signal in order to measure changes in magnitude of the flaw signal with respect to rotation angles and to compare the measured changes with those obtained in advance with respect to flaws of a standard flaw test piece.

DESCRIPTION OF THE PREFERRED EMBODIMENT

Figure 1:
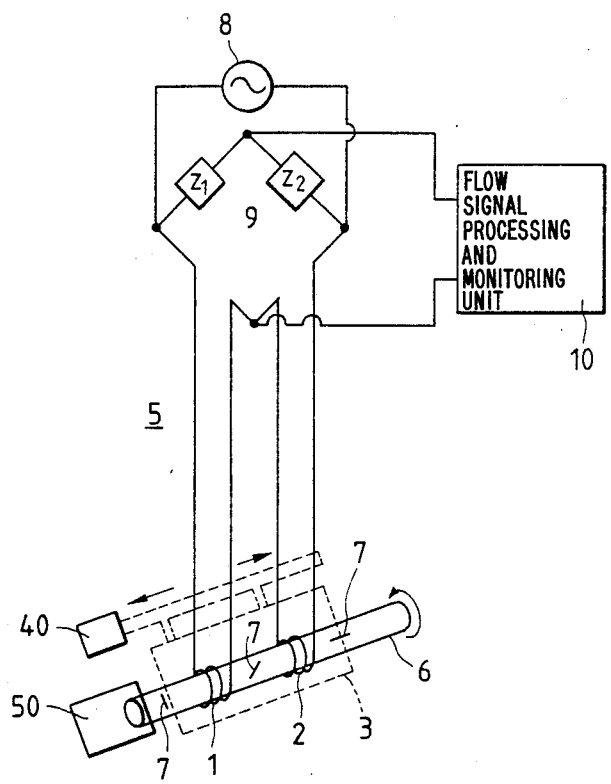
FIG. 1 is a schematic view of one embodiment of an eddy current flaw detecting apparatus according to the present invention.

The present invention will be explained with reference to an embodiment shown in FIGS. 1, 2 and 3.

The eddy current flaw detecting apparatus according to the present invention will be explained with reference to FIG. 1. The reference numerals 1 and 2 represent inclined through type detecting coils, 3 a coil housing, 6 a fuel clad pipe, the object being examined, 7 flaws or scratchs in the fuel clad pipe 6, 8 a high-frequency oscillator, 9 a bridge circuit, 10 a flaw signal processing and monitoring unit, 40 a coil driving device, and 50 a device for rotating the fuel clad pipe 6 being examined. The arrows in FIG. 1 indicate moving directions of the coil housing 3 and the rotating direction of the fuel clad pipe 6.

Figure 2:
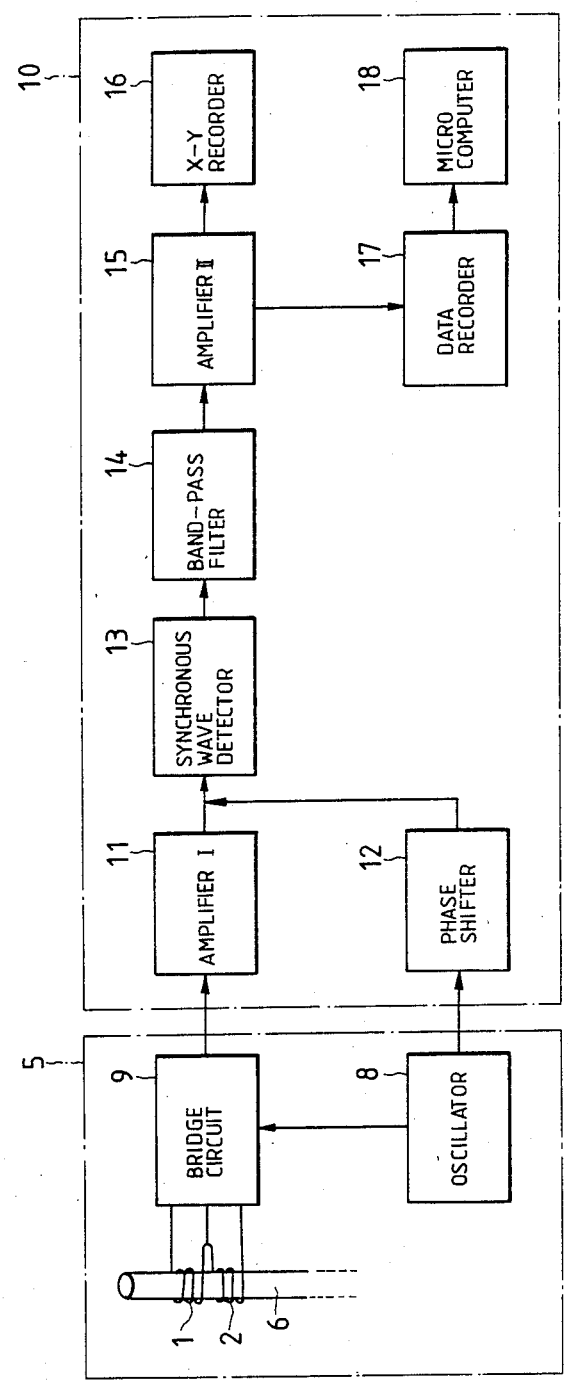
FIG. 2 is a block diagram of a flaw detecting bridge circuit unit and a flaw signal processing and monitoring unit included in the embodiment shown in FIG. 1.

FIG. 2 shows a block diagram of a flaw detecting bridge circuit unit 5 and a flaw signal processing and monitoring unit 10. The flaw detecting bridge circuit unit 5 comprises a bridge circuit 9 and an oscillator 8 which supplies a high frequency current such as 128 KHz and 256 KHz to the bridge circuit 9.

To the adjoining arms of the bridge circuit 9 the pair of inclined detecting coils 1 and 2 are connected as shown in FIG. 1. The flaw signal processing and monitoring unit 10 comprises an amplifier I 11, a phase shifter 12, a synchronous wave detector 13, a band-pass filter 14, an amplifier II 15, an X-Y recorder 16, a data recorder 17 and a micro computer 18. The amplifier I 11 amplifies small output signals representing flaws from the bridge circuit 9. The output signals from the amplifier I 11 are applied to the synchronous wave detector 13 wherein the input signals are phase-analyzed by control signals applied from the phase shifter 12 in other words, a phase shift of the flaw signal from the applied high frequency current is determined.

The band-pass filter 15 eliminates noise components in the flaw signals, the filtered flaw signals are again amplified with the amplifier II 15 and applied therefrom to the X-Y recorder 16 and the data recorder 17. The flaw signals in the data recorder 17 are transferred to the micro computer 18 wherein the position, type, size and direction of flaws in the object being examined are determined by comparing flaw signal characteristics obtained in advance with respect to standard flaw testing pieces.

Figure 3:
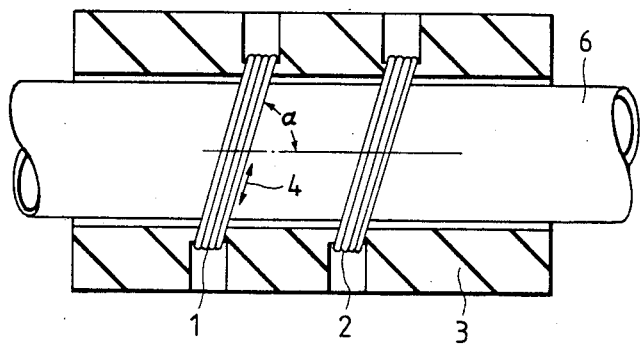
FIG. 3 is a sectional view of a pair of detecting coils unit included in the embodiment shown in FIG. 1, wherein an object being examined is inserted through the pair of detecting coils unit.

FIG. 3 shows an arrangement and disposition of the pair of detecting coils 1 and 2 constituting adjoining arm elements of the flaw detecting bridge circuit 9. The planes containing the pair of detecting coils 1 and 2 are arranged in parallel and inclined to the axis of the fuel clad pipe 6 with an inclination angle $\alpha$ which is preferably in a range between 75° and 85°. When a more acute inclination angle is selected, separation ability of the flaw detecting bridge circuit unit between circumferential flaw signals and axial flaw signals is improved, however, areas covered by the magnetic flux induced by the pair of detecting coils on the fuel clad pipe being examined increase so that noise level may exceeds that of flaw signals representing comparatively shallow flaws such that the detection ability of the flaw detecting bridge circuit unit decreases.

The numeral 4 indicates the direction of eddy current flowing on the fuel clad pipe 6 induced by the pair of detecting coils. Since the direction of the eddy current is inclined so that detection and separation of the circumferential flaws from the axial flaws is facilitated.

Principle of the present invention is explained herein below.

During experimental study of the present invention, a fuel clad pipe for light-water type power reactors (12 mm in outer diameter, 0.86 mm in wall thickness and about 4,000 mm in length made of zircalloy-2, hereinunder referred to as "clad pipe") was used as an example of an object being examined.

Figure 4A:
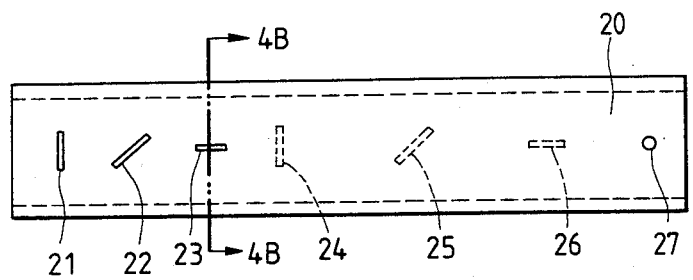
FIG. 4A is a side view of a standard flaw test piece used in connection with the present invention.
Figure 4B:
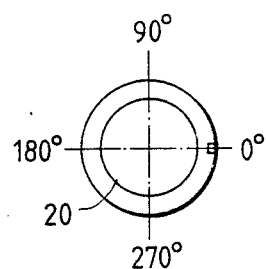
FIG. 4B is a cross sectional view taken along line 4B—4B of FIG. 4A.

Determination of the circumferential position, type and size of flaws with the eddy current flaw detecting apparatus, which is however conventional, will first be explained. FIGS. 4A and 4B shows a schematic view of a standard flaw testing piece provided with artificial flaws such as external, internal, axial, circumferential and through hole flaws. In FIG. 4A, the reference numeral 20 represents a standard flaw testing piece clad pipe, 21 an external circumferential flaw, 22 a flaw in the direction of 45 degrees on the outer surface, 23 an external axial flaw, 24 an internal circumferential flaw, 25 a flaw in the direction of 45 degrees on the inner surface, 26 an internal axial flaw, and 27 a through hole flaw. FIG. 4B shows a vertical section of the clad pipe, and illustrates the relative turning angle position of the clad pipe wherein the circumferential position of the artificial flaw location is defined as a reference position, in that, turning angle $\theta$ of 0°.

Figure 5:
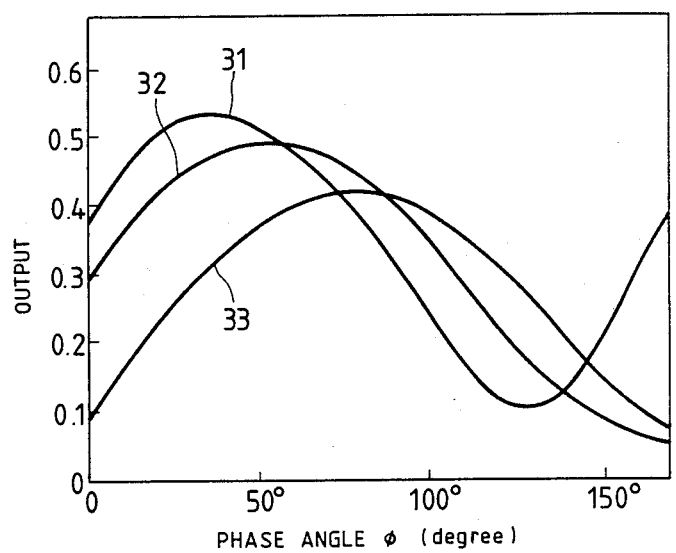
FIG. 5 illustrates relationships between flaw signal magnitudes and phase angles $\Phi$ obtained with the standard flaw test piece shown in FIGS. 4A and 4B.

In the pair detection coils of the eddy current flaw detecting apparatus, a standard flaw detecting piece such as that shown in FIGS. 4A and 4B was set, and a phase angle of a phase shifter 12 included in a flaw signal processing and monitoring unit 10 was changed by 10 degrees from 0 to 180 degrees so as to measure the flaw signal output (V) for each 10 degrees from a flaw detecting bridge circuit 9, thereby obtaining phase characteristic curves of the flaw signals such as those shown in FIG. 5. In FIG. 5, the reference numeral 31 denotes a characteristic curve of an external circumferential flaw 21, wherein the maximum flaw signal output is at a phase angle of about 30 degrees, 32 denotes a characteristic curve of a through hole flaw 27, wherein the maximum output is at a phase angle of about 50 degrees, and 33 denotes a characteristic curve of an internal circumferential flaw 24, wherein the maximum output is at a phase angle of about 80 degrees. The phase angles of these maximum outputs are dependent upon the oscillating frequency of the flaw detecting bridge circuit unit and the packing ratio of the inner diameter of the coils and the outer diameter of the clad pipe and is independent of the size of the flaw. In the same way, phase characteristic curves of flaw signals with regard to axial flaws 23 and 26 were obtained.

Figure 6:
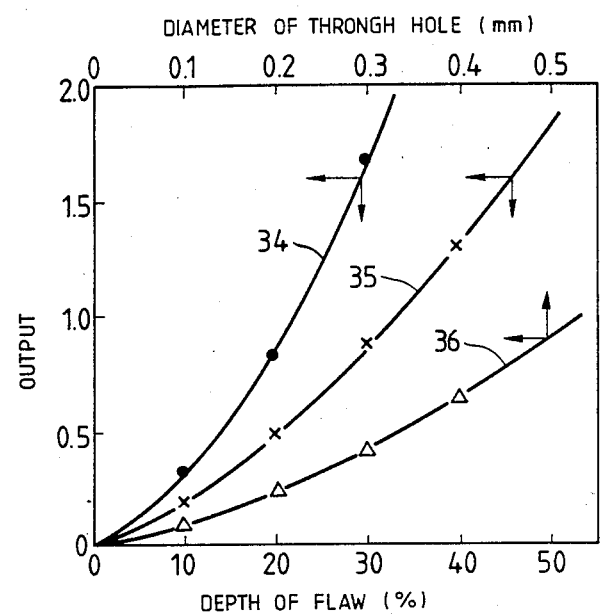
FIG. 6 illustrates relationships between flaw signal magnitudes and depth of flaws and diameter of through holes obtained with the standard flaw test pieces shown in FIGS. 4A and 4B.

In order to detect the size, in other words, depth of a flaw and diameter of a through hole, several standard flaw testing pieces such as that shown in FIGS. 4A and 4B having different depths, of from 0 to 50% and different diameters were prepared. The relationships between the depth (%) of a flaw and the flaw signal output (V) of an external flaw, an internal flaw and a through hole flaw, respectively, were plotted at the respective phases $\Phi$ for producing the maximum outputs by using the several testing pieces having different flaw depths and through hole diameters. The results are shown in FIG. 6. In FIG. 6, the reference numeral 34 represents the relationship between the depth of the external circumferential flaw 21 and the flaw signal output and 35 the relationship between the depth of the internal circumferential flaw 24 and the flaw signal output. The reference numeral 36 represents the relationship between the diameter of the through hole flaw and the flaw signal output (V).

On the basis of these relationships, it is possible to judge the position, type, in that, external flaw, internal flaw or through hole flaw, and size of a flaw in the clad pipe are determined.

In a conventional eddy current flaw detecting apparatus having a pair of detecting coils for a flaw detecting bridge circuit unit, of which planes are in parallel and not inclined, in that, 90°, to the longitudinal axis, when the standard flaw testing pieces 20 having an external circumferential flaw 21, an external axial flaw 22 and a through hole flaw 27, respectively, were subject to measurement while rotating them at a turning angle $\theta$ of 0° to 360° in the magnetic field of the pair of detecting coils, the respective flaw signal outputs showed constant values irrespective of the turning angle.

However, when they were measured with the eddy current flaw detecting apparatus of the present invention having a pair of detecting coils for a flaw detecting bridge circuit unit, of which planes are in parallel and inclined to the longitudinal axis of the standard flaw testing piece 20 with an inclination angle α, a very remarkable phenomenon was observed.

The results of these experimental study will now be explained with reference to FIG. 7.

Figure 7:
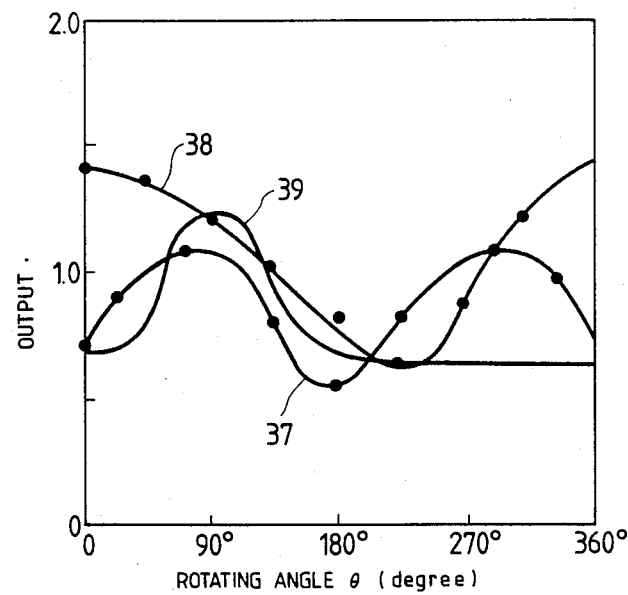
FIG. 7 illustrates relationships between flaw signal magnitudes and relative rotation angles $\theta$ from a reference point of the pair of detection coils obtained with respect to the standard flow test pieces shown in FIGS. 4A and 4B.

When the external circumferential flaw 21 in the standard flaw testing piece 20 was subjected to the rotational test from the reference point 0° to 360° as shown in FIG. 4B with the phase angle of 30° wherein the maximum flaw signal output is produced as indicated in FIG. 5, the magnitude of the flaw signal output changed as illustrated by a characteristic curve 37 shown in FIG. 7, in that, the characteristic curve having two flaw signal output peaks at turning angles of about 90° and 270°. Similarly, with the external axial flaw 23 in the standard flaw testing piece 20, a characteristic curve 38 having a trough in the vicinity of the turning angle 230° was obtained as illustrated in FIG. 7. Flaw signal output change of the through hole flaw 27 in the standard flaw testing piece 20 was also measured while rotating the standard flaw testing piece 20 from a reference point of 0° to 360°, the results are illustrated by a characteristic curve 39 shown in FIG. 7.

Although not illustrated, substantially similar characteristic curves as those illustrated in FIG. 7 were obtained with respect to the internal circumferential and axial flaws 24 and 26 in the standard flaw testing piece 20.

It was further confirmed by the experimental study that characteristic curves of flaws having intermediate direction between circumferential and axial directions showed intermediate characteristic curves, in other words it was confirmed that the characteristic curves vary uninterruptedly from the characteristic curve 37 to that 38 depending upon flaw directions.

A flaw detecting operation with the eddy current flaw detecting apparatus according to the present invention indicated above will be explained hereinafter;

The fuel clad pipe 6 being examined is first inserted into the inclined through type pair of coils 1 and 2, and the high frequency oscillator 8 is switched on so as to induce eddy current in the fuel clad pipe 6. The inclined through type coils 1 and 2 are moved along the fuel clad pipe 6 by the coil driving device 40 until a flaw signal is detected by the flaw signal detecting bridge circuit unit 5 while monitoring signals from the bridge circuit unit 5 with the flaw signal processing and monitoring unit 10, when a flaw signal is detected, the movement of the coils is stopped and phase angle Φ of the phase shifter 12 in the flaw signal processing and monitoring unit 10 is shifted by 10° from 0° to 180° to obtain the relationship between flaw signal output and phase angle to determine the type of the flaw, such as external, internal and through hole flaws, with reference to the characteristic curves obtained in advance with respect to the standard flaw testing pieces exemplarily illustrated in FIG. 5.

For example, when the flaw is determined to be an external flaw, the phase angle of the phase shifter 12 is set at about 30° where the flaw signal output from the bridge circuit unit 5 is maximum and the fuel clad pipe 6 is rotated by 10° from 0° to 360° by the rotating device 50 to obtain the relationship between flaw signal output and turning angle to determined the direction of the flaw such as circumferential, axial and intermediate thereof with reference to the characteristic curves obtained in advance with respect to the standard flaw testing pieces exemplarily illustrated in FIG. 7.

Although, this embodiment is applied to a fuel clad pipe, it is also applicable to other pipes, tubes and wires by modifying a part of this embodiment.

In addition, this embodiment is used in air, but it is also usable, for example, in a water pool in an nuclear power plant.

In this embodiment, the object being examined is rotated in the inclined through type coils 1 and 2 by using the device 50 for rotating an object being examined. Conversely, it is also possible to measure the relationship between the turning angle and the flaw signal output by rotating the inclined through type coils 1 and 2 around the object being examined.

We claim:

1. An eddy current flaw detecting method comprising the steps of:
    moving an object being examined relative to and through a pair of detecting coils, each connected in adjoining arms of a bridge circuit outputting signals representing flaws in the object being examined, the planes containing the pair of detecting coils being arranged in parallel and inclined to the longitudinal axis of the object being examined with a predetermined angle;
    stopping the relative movement of the object being examined when the bridge circuit outputs signals representing flaws;
    rotating the object being examined relative to the pair of detecting coils to measure changes in magnitude of the signals representing the flaws;
    comparing the measured changes in magnitude of the signals representing the flaws with changes in magnitude of signals obtained in advance with flaws of a standard flaw test piece, thereby determining a direction of the detected flaws in the object being examined;
    wherein the predetermined inclination angle of the planes containing the pair of detecting coils is in a range between 75° and 85°; and
    further comprising the step of adjusting a phase angle of a phase shifter in a flaw signal processing and monitoring unit so as to maximize the signals representing flaws being output from a synchronous wave detector in the flaw signal processing and monitoring unit before said rotating step.

* * * * *